United States Patent [19]

Borgarello et al.

[11] Patent Number: 5,055,610

[45] Date of Patent: Oct. 8, 1991

[54] PROCESS FOR THE SEPARATION OF SULPHURIC ACID FROM AQUEOUS MIXTURES THEREOF WITH PARAFFIN-SULPHONIC ACIDS

[75] Inventors: Enrico Borgarello, Turin; Lucio Faggian; Edoardo Platone, both of Milan; Cosimo Franco, Locri, all of Italy

[73] Assignees: Eniricerche S.p.A., Milan; Enichem Augusta S.p.A., Palermo, both of Italy

[21] Appl. No.: 546,015

[22] Filed: Jun. 28, 1990

Related U.S. Application Data

[63] Continuation of Ser. No. 136,852, Dec. 12, 1987, abandoned.

[30] Foreign Application Priority Data

Dec. 23, 1986 [IT] Italy ............................... 22816 A/86

[51] Int. Cl.$^5$ ............................................ C07C 143/02
[52] U.S. Cl. .................................. 562/124; 252/182.3; 562/33
[58] Field of Search ................. 252/182.3; 260/504 R, 260/504 S, 513 R, 513 T; 562/124, 33

[56] References Cited

U.S. PATENT DOCUMENTS

| | | | |
|---|---|---|---|
| 2,263,041 | 11/1941 | Lazar et al. | 260/504 S |
| 2,530,757 | 11/1950 | Bransky et al. | 260/504 S |
| 3,164,547 | 1/1965 | Brunel et al. | 260/504 R |
| 4,178,307 | 12/1979 | Boy et al. | 260/504 S |
| 4,310,473 | 1/1982 | Springmann et al. | 260/504 S |
| 4,321,214 | 3/1982 | Nicolet | 260/504 S |
| 4,456,564 | 6/1984 | Stapp | 260/504 S |
| 4,557,873 | 12/1985 | Pistorius | 260/513 R |
| 4,652,343 | 3/1987 | Sridhar | 260/513 R |
| 4,680,147 | 7/1987 | Pistorius | 260/504 S |
| 4,808,343 | 2/1989 | Pistorius | 562/124 |

*Primary Examiner*—Edward A. Miller
*Attorney, Agent, or Firm*—Morgan & Finnegan

[57] ABSTRACT

The mixture from which sulphuric acid must be separated according to the present invention are those which derive from the sulphoxidation of $(C_{12}-C_8)$-n-paraffins with $SO_2$ and $O_2$ in the presence of water and of U.V. light at a temperature comprised within the range of from 25 to 50° C., after the removal of n-paraffins, which separate spontaneously, and of $SO_2$ excess. In order to remove said sulphuric acid, the refined mixture, possibly diluted with water, is mixed with one or more halogenated solvents, the separation being obtained of water and sulphuric acid from the refined mixture, to the total mixture (with the two phases) a cosolvent is added, which is constituted by alcohols or ethers, with the separation being obtained of a phase constituted by $H_2O$ and $H_2SO_4$, which is removed. The residual organic phase, practically free from sulphuric acid, is submitted to the removal of solvents and cosolvents by means of conventional techniques.

14 Claims, No Drawings

PROCESS FOR THE SEPARATION OF SULPHURIC ACID FROM AQUEOUS MIXTURES THEREOF WITH PARAFFIN-SULPHONIC ACIDS

This is a continuation of co-pending application Ser. No. 07/136,852 filed Dec. 22, 1987, now abandoned.

The present invention relates to a process for the separation of sulphuric acid from aqueous mixtures thereof with paraffin-sulphonic acids.

The mixtures from which sulphuric acid must be separated according to the present invention are those which derive from the sulphoxidation of ($C_{12}$–$C_{18}$)-n-paraffins with $SO_2$ and $O_2$ in the presence of water and of U.V. light at a temperature comprised within the range of from 25° to 50° C., after the removal of n-paraffins, which separate spontaneously, and of the excess of $SO_2$, and after being submitted to one of the following treatments:

a) dehydration, by known systems, of the residual mixture, at least until said mixture becomes cloudy (due to the formation of a biphasic system), extraction of not-sulphoxidated paraffins from the dehydrated, cloudy mixture, or from the supernatant phase of the biphasic system, with supercritical $CO_2$ at a temperature comprised within the range of from 32° C. to 80° C., under a pressure comprised within the range of from 75 to 350 bars, and with a $CO_2$/paraffin-sulphonic acids weight ratio of from 1/1 to 50/1.

b) addition of $H_2SO_4$ to the residual mixture, at least until said mixture becomes cloudy (due to the formation of a biphasic system), extraction, with supercritical $CO_2$, from the cloudy mixture or from the supernatant phase of the biphasic system, of the residual paraffins under such conditions as shown under (a);

c) addition to the residual mixture of an aliphatic alcohol containing a number of carbon atoms lower than, or equal to, 4, preferably isopropanol, until a biphasic mixture is formed, extraction from said biphasic mixture of the residual paraffins with supercritical $CO_2$ under such conditions as reported under (a).

The mixture of paraffin-sulphonic acids free, or substantially free, from paraffins, obtained by means of the above disclosed treatments from (a) to (c) (the "refined mixture") still contains, besides the paraffin-sulphonic acids, a considerable amount of $H_2SO_4$.

The purpose of the process of the present invention is to remove said excess of sulphuric acid.

The compositions of the refined mixtures of paraffin-sulphonic acids obtained by means of the methods herein previously mentioned from (a) to (c) are the following:

1) ($C_{12}$–$C_{18}$)-Paraffin-sulphonic acids: from 3 to 83% by weight;
2) $H_2O$: from 79 to 8.5% by weight;
3) $H_2SO_4$: from 18 to 8.5% by weight;
4) ($C_{12}$–$C_{18}$)-Paraffins: less than 1% relatively to ($C_{12}$–$C_{18}$)-paraffin-sulphonic acids.

Obviously, the starting mixture, even if is obtained by the present Applicants in the above 3 ways, can be obtained in other ways too, so that the present invention should not be considered as being limited to the way in which the starting mixture with the above reported composition is obtained, in as much as the process of the invention can be applied to any mixtures, in whatever way they are obtained, having the above compositions.

The process according to the present invention comprises mixing the refined mixture, having the above-said compositions, at a temperature comprised within the range of from 10° to 80° C., preferably of from 20° to 50° C., with one or more halogenated solvent(s) selected from those complying with the general formulae (1), (2), (3):

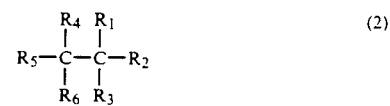

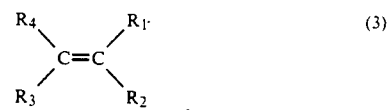

wherein at least one of $R_1$, $R_2$, $R_3$, $R_4$, $R_5$, $R_6$ is a halogen, the other R radicals being H, the halogen being fluorine and/or chlorine and/or bromine and/or iodine, with two phases being formed, one of which is essentially organic, and the other is constituted by $H_2SO_4$ and $H_2O$; to the two phases, together with each other, at least one cosolvent is added, which is selected from the class of the lower, saturated, linear or branched alcohols with from 1 to 6 carbon atoms, or of the lower, linear, branched or cyclic or possibly substituted aliphatic ethers with a number of carbon atoms comprised within the range of from 2 to 10, with the separation being obtained of a phase which is constituted by $H_2SO_4$ and $H_2O$, which is removed. The residual organic phase, practically free from $H_2SO_4$, is submitted to the removal of the solvents and cosolvents, in particular by distillation at a temperature lower than 100° C., preferably lower than 50°–60° C., still more preferably at least partially under vacuum.

Relatively to the refined mixture, the amount of solvent is in a weight ratio comprised within the range of from 0.5/1 to 5/1, and the amount of cosolvent is, relatively to the refined mixture, in a weight ratio comprised within the range of from 0.3/1 to 2/1.

The temperature at which the cosolvent is added is comprised within the range of from 10° to 80° C., preferably of from 20° to 50° C. According to a form of practical embodiment of the process according to the present invention, the halogenated solvent(s) and the cosolvent can be simultaneously mixed with the refined mixture in a single step.

Among the halogenated solvents preferred are methylene chloride, chloroform, carbon tetrachloride and dichloroethane.

Among alcohols, preferred are methanol, ethanol, propanol, isopropanol, butanols, pentanols, and among ethers, preferred are dimethyl-ether, diethyl-ether, dipropyl-ether, diisopropyl-ether, methyl-tert.-butyl-ether, tetrahydrofuran and mono-, di-, tri- and tetramethyl-hydrofurans.

Residual $H_2SO_4$, if any, or, partially, $H_2SO_4$ present before the application of the process according to the present invention, can be removed by being converted into an insoluble product by means of the addition of carbonates, hydroxides or oxides of alkaline-earth metals, in particular, by the addition of calcium carbonate, hydroxide or oxide.

Some examples are now given for the purpose of better illustrating the invention, it being understood that it has not to be considered as being limited to them or by them.

EXAMPLE 1

To a large glass test tube, tightly sealable, 2.1012 g is charged of a mixture having the following composition:

| | |
|---|---|
| Paraffin-sulphonic acids | 59.95% by weight |
| $(C_{12}-C_{18})$-n-paraffins | 0.22% by weight |
| Water | 28.72% by weight |
| Sulphuric acid | 11.11% by weight |

It had been obtained by means of the extraction with supercritical $CO_2$ of the n-paraffins contained in the upper phase of a raw mixture (from which the decantable n-paraffins and $SO_2$ had been removed) of paraffin-sulphonic acids, obtained by means of the sulphoxidation of $(C_{12}-C_{18})$-n-paraffins, having the following composition:

| | |
|---|---|
| Paraffin-sulphonic acids | 24.74% by weight |
| $(C_{12}-C_{18})$-n-paraffins | 26.46% by weight |
| Water | 40.94% by weight |
| Sulphuric acid | 7.86% by weight | after extraction with 20% by weight of $H_2SO_4$ at 96% by weight, referred to the weight of said raw mixture, as reported in U.S. patent application Ser. No. 071,872.

The above-said mixture, having an $H_2SO_4$/paraffin-sulphonic acids weight ratio of 18.5%, is treated, at room temperature (20°–22° C.) with 1.9013 g of $H_2O$, and subsequently, with 6.4562 g of methylene chloride.

The mixture is intensely shaken for a few minutes, and is left standing for half an hour. Thus, two phases separate from each other, the upper of which contains all of the paraffin-sulphonic acids together with water, sulphuric acid, the initially present n-paraffins and methylene chloride; and the lower phase contains a few methylene chloride, water and sulphuric acid. In particular, the content of sulphuric acid, referred to the paraffin-sulphonic acids in the upper phase, is reduced from 18.5% to 11%.

Subsequently, without separating the phases, 1,3401 g of ethyl alcohol is added, the test tube is intensely shaken and is left standing for half an hour.

The lower phase contains all of the paraffin-sulphonic acids together with a few water, the initially present n-paraffins, methylene chloride and ethyl alcohol, and the upper phase contains sulphuric acid, water and ethyl alcohol.

From the analyses, the weight ratio of sulphuric acid/paraffin-sulphonic acids, in the organic phase, results to have been reduced from 11% to 1.5%.

EXAMPLE 2

1.9173 g of a mixture having the same composition as used in Example 1, is treated, at room temperature (20°–22° C.) with 1.7349 g of $H_2O$, and subsequently, with 8.6370 g of a (3:1 by weight) methylene chloride/ethyl alcohol mixture.

The whole mixture is intensely shaken and is centrifuged for 15 minutes. The lower phase contains all of the paraffin-sulphonic acids together with a few water, the initially present n-paraffins, methylene chloride and ethyl alcohol; and the upper phase contains sulphuric acid, water and ethyl alcohol.

From the analyses, the weight ratio of sulphuric acid/paraffin-sulphonic acids, in the organic phase, results to have been decreased from 18.5% to 1.8%.

EXAMPLE 3

20.85 g of a mixture having the same composition as used in Example 1, is treated, at room temperature (23° C.) with 18.85 g of $H_2O$, with 64.00 g of methylene chloride, and with 13.30 g of ethanol. The mixture is intensely shaken and is centrifuged for 15 minutes.

The lower phase contains all of the paraffin-sulphonic acids together with a few water, the initially present n-paraffins, methylene chloride and ethyl alcohol; and the upper phase contains sulphuric acid, water and ethyl alcohol.

The two phases are separated from each other. The lower phase is evaporated inside a rotary evaporator, so as to distill off all of the solvents, by operating with the heating bath being kept at 70° C. (75° C. during the last 5 minutes), and under a progressively increasing vacuum up to 750 $mm_{Hg}$ during the end step.

The distillation residue is a thin liquid essentially constituted by paraffin-sulphonic acids, 4.91% by weight of $H_2O$, 1.84% by weight of $H_2SO_4$ and 0.337% by weight of $(C_{12}-C_{18})$-n-paraffins.

The distribution of monosulphonic, disulphonic and trisulphonic acids in the concentrated end product results to be the same as of the raw mixture of paraffin-sulphonic acids downstream the sulphoxidation reactor.

EXAMPLES 4 TO 21

By operating according to the same modalities as reported in the preceding Examples, different tests were carried out, with the solvent and the cosolvent being varied both in type and in amount. All the tests were carried out by using the mixture of paraffin-sulphonic acids as used in Example 1.

The results obtained are shown in the following Table.

TABLE

| EXAMPLE No. | PROCEDURE | MIXTURE grams | $H_2O$ grams | Solvent Type | Grams | Cosolvent Type | Grams | Sulphuric Acid / Paraffin-sulphonic acid % RATIO |
|---|---|---|---|---|---|---|---|---|
| 4 | see Example 2 | 2.1866 | 0.6119 | $CH_2Cl_2$ | 6.5806 | EtOH | 1.2712 | 4.5 |
| 5 | see Example 1 | 2.3924 | 2.2497 | $CH_2Cl_2$ | 6.3548 | i-Pr—OH | 1.4826 | 1.5 |
| 6 | see Example 1 | 2.0655 | 2.0693 | $CH_2Cl_2$ | 6.6429 | 1-$C_5$—OH | 1.4314 | 0.9 |
| 7 | see Example 1 | 2.3771 | 1.8852 | $CH_2Cl_2$ | 6.6885 | MeOH | 0.6151 | 3.7 |
| 8 | see Example 1 | 2.2188 | 2.7099 | $CH_2Cl_2$ | 6.5786 | MeOH | 0.5362 | 4.5 |
| 9 | see Example 2 | 2.0640 | 1.9410 | $CH_2Cl_2$ | 6.5875 | MeOH | 1.3528 | 4.6 |
| 10 | see Example 2 | 1.9923 | 2.6961 | $CH_2Cl_2$ | 6.5955 | EtOH | 1.3102 | 3.8 |
| 11 | see Example 2 | 1.8997 | 1.6804 | $CH_2Cl_2$ | 6.5972 | EtOH | 0.7412 | 3.1 |
| 12 | see Example 1 | 3.72 | 5.05 | $CH_2Cl_2$ | 13.25 | MeOH | 0.79 | 4.4 |
| 13 | see Example 1 | 17.90 | 5.11 | $CH_2Cl_2$ | 59.62 | MeOH | 0.42 | 11.1 |

TABLE-continued

| EXAMPLE No. | PROCEDURE | MIXTURE grams | H$_2$O grams | Solvent Type | Solvent Grams | Cosolvent Type | Cosolvent Grams | $\frac{\text{Sulphuric Acid}}{\text{Paraffin-sulphonic acid}}$ % RATIO |
|---|---|---|---|---|---|---|---|---|
| 14 | see Example 1 | 8.52 | 6.12 | CH$_2$Cl$_2$ | 59.67 | MeOH | 2.60 | 7.3 |
| 15 | see Example 1 | 4.31 | 5.10 | CH$_2$Cl$_2$ | 13.25 | MeOH | 0.41 | 16.5 |
| 16 | see Example 1 | 53.0 | 60.7 | CH$_2$Cl$_2$ | 159.2 | MeOH | 12.0 | 8.16 |
| 17 | see Example 1 | 5.0 | 6.2 | CH$_2$Cl$_2$ | 17.22 | MeOH | 1.2 | 9.9 |
| 18 | see Example 2 | 5.0 | 11.0 | CH$_2$Cl$_2$ | 28.22 | MeOH | 2.0 | 8.5 |
| 19 | see Example 3 | 2.3598 | 2.2735 | CH$_2$Cl$_2$ | 7.2314 | EtOH | 1.6936 | 3.68 |
| 20 | see Example 3 | 2.4588 | 2.3136 | CH$_2$Cl$_2$ | 7.6327 | THF | 1.5563 | 2.4 |
| 21 | see Example 3 | 2.6843 | 2.5680 | CH$_2$Cl$_2$ | 8.4993 | ET$_2$O | 1.8499 | 4.2 |

EtOH = ethanol; MeOH = methanol; 1-C$_5$—OH = 1-pentanol; i-Pr—OH = isopropanol; THF = tetrahydrofuran; Et$_2$O = diethyl ether

We claim:

1. A process for the separation of sulfuric acid from aqueous mixtures thereof with (C$_{12}$-C$_{18}$)-paraffin-sulfonic acids, wherein said aqueous mixtures comprise:
   (a) from 3 to 83% by weight of (C$_{12}$-C$_{18}$)-paraffin-sulfonic acids;
   (b) from 8.5 to 79% by weight of water;
   (c) from 8.5 to 18% by weight of H$_2$SO$_4$; and
   (d) less than 1% by weight, relative to (C$_{12}$-C$_{18}$)-paraffin-sulfonic acids, of (C$_{12}$-C$_{18}$)-paraffins, said process consisting essentially of the steps of:
   (a) mixing the aqueous mixture, at a temperature within the range of 10° to 80° C., with one or more halogenated solvent(s), selected from the group consisting halogenated derivatives of methane, ethane and ethylene of the formula (1), (2) or (3):

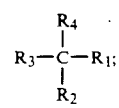

(1)

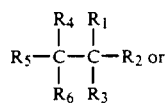

(2)

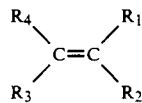

(3)

wherein R$_1$, R$_2$, R$_3$, R$_4$, R$_5$ and R$_6$ each independently is hydrogen or halogen, at least one of R$_1$, R$_2$, R$_3$, or R$_4$ in formula (1) or (3) is halogen or at least one R$_1$, R$_2$, R$_3$, R$_4$, R$_5$ or R$_6$ in formula (2) is halogen so as to form a two phase mixture of an aqueous phase containing sulfuric acid and an organic phase;
   (b) adding a co-solvent to the two phase mixture of step (a), the co-solvent being selected from the group consisting of straight or branched, saturated, (C$_1$-C$_6$) alcohols, straight, branched or cyclic aliphatic ethers with from 2 to 10 carbon atoms and mixtures thereof so as to form an aqueous phase and an organic phase;
   (c) separating the aqueous phase of step (b) from the organic phase of step (b); and
   (d) submitting the separated organic phase of step (c) to a treatment of separation so as to remove therefrom the co-solvent and halogenated solvents and to obtain (C$_{12}$-C$_{18}$)-paraffin sulfonic acids practically free of sulfuric acid.

2. A process according to claim 1, wherein said aqueous mixture is diluted with H$_2$O before step (a).

3. A process according to claim 1, wherein said halogenated solvent in step (a) is selected from the group consisting of chloroform, methylene chloride, carbon tetrachloride and dichloroethane.

4. A process according to claim 1, wherein said co-solvent of step (b) is selected from the group consisting of methanol, ethanol, 1-propanol, isopropanol, butanols, pentanols, dimethyl-ether, diethyl-ether, dipropyl-ether, diisopropyl-ether, methyl-tert butyl-ether, tetrahydrofuran, and mono-, di-, and tetramethyl-tetrahydrofurans.

5. A process according to claim 1, wherein the ratio, by weight, of said halogenated solvent and said aqueous mixture, is from about 0.5:1.

6. A process according to claim 1, wherein the ratio, by weight, of the co-solvent and the aqueous mixture, is from about 0.3:1 to 2:1.

7. A process according to claim 1, wherein the temperature of step (a), is from 20° to 50° C.

8. A process according to claim 1, wherein the treatment of separation in step (d) is distillation at a temperature of up to 100° C.

9. A process according to claim 8, wherein the temperature in step (d) is up to 60° C.

10. A process according to claim 1, wherein said treatment of separation in step (d) is vacuum distillation.

11. A process according to claim 1, further comprising the step of:
   (e) adding to the organic phase of step (c), alkaline-earth metal carbonates, hydroxides or oxides so as to insolubilize any H$_2$SO$_4$ still present.

12. A process according to claim 1, wherein the addition of said co-solvent according to step (b) is carried out at a temperature from 10° to 80° C.

13. A process according to claim 12, wherein the temperature in step (b) is from 20° to 50° C.

14. A process for the separation of sulfuric acid from aqueous mixtures thereof with (C$_{12}$-C$_{18}$) paraffin-sulfonic acids, wherein said aqueous mixtures comprise:
   (a) from 3 to 83% by weight of (C$_{12}$-C$_{18}$)-paraffin-sulfonic acids;
   (b) from 8.5 to 79% by weight of water;
   (c) from 8.5 to 18% by weight of H$_2$SO$_4$; and
   (d) less than 1% by weight, relative to (C$_{12}$-C$_{18}$)-paraffin-sulfonic acids, of (C$_{12}$-C$_{18}$)-paraffin, said process consisting essentially of the steps of:
   (a) mixing the aqueous mixture, at a temperature within the range from 10° to 80° C., with one or more halogenated solvent(s), selected from the group consisting of halogenated derivatives of methane, ethane and ethylene of the formula (1), (2) or (3):

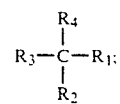

(1)

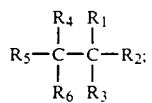

(2)

or

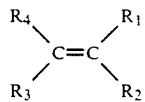

(3)

wherein $R_1$, $R_2$, $R_3$, $R_4$, $R_5$ and $R_6$ each independently is hydrogen or halogen, at least one of $R_1$, $R_2$, $R_3$ or $R_4$ in formula (1) or (3) is halogen or at least one $R_1$, $R_2$, $R_3$, $R_4$, $R_5$ or $R_6$ in formula (2) is halogen and with a co-solvent selected from group consisting of straight or branched, saturated $(C_1-C_6)$ alcohols, straight, branched, or cyclic aliphatic ethers with from 2 to 10 carbon atoms and mixtures thereof so as to form a two phase mixture of an aqueous phase containing sulfuric acid and organic phase;

(b) separating the aqueous phase from the organic phase obtained from step (a); and (c) submitting the separated organic phase obtained from step (b) to a treatment of separation so as to remove the co-solvent and halogenated solvent and to obtain $(C_{12}-C_{18})$-paraffin sulfonic acids practically free of sulfonic acid.

* * * * *